(12) United States Patent
Younis

(10) Patent No.: US 8,168,120 B1
(45) Date of Patent: May 1, 2012

(54) RELIABLE SWITCH THAT IS TRIGGERED BY THE DETECTION OF A SPECIFIC GAS OR SUBSTANCE

(75) Inventor: Mohammad Younis, Johnson City, NY (US)

(73) Assignee: The Research Foundation of State University of New York, Binghamton, NY (US)

( * ) Notice: Subject to any disclaimer, the term of this patent is extended or adjusted under 35 U.S.C. 154(b) by 1044 days.

(21) Appl. No.: 12/043,871

(22) Filed: Mar. 6, 2008

Related U.S. Application Data

(60) Provisional application No. 60/943,303, filed on Jun. 11, 2007, provisional application No. 60/893,342, filed on Mar. 6, 2007.

(51) Int. Cl.
*G01N 33/00* (2006.01)

(52) U.S. Cl. .................. 422/82.01; 422/68.1; 422/82.02

(58) Field of Classification Search .................. 422/68.1, 422/82.01, 82.02
See application file for complete search history.

(56) References Cited

U.S. PATENT DOCUMENTS

| | | | |
|---|---|---|---|
| 5,116,462 A | 5/1992 | Bartha et al. |
| 5,171,992 A | 12/1992 | Clabes et al. |
| 5,272,913 A | 12/1993 | Toda et al. |
| 5,282,924 A | 2/1994 | Bayer et al. |
| 5,445,008 A | 8/1995 | Wachter et al. |
| 5,455,419 A | 10/1995 | Bayer et al. |
| 5,580,827 A | 12/1996 | Akamine |
| 5,663,507 A | 9/1997 | Westervelt et al. |
| 5,670,712 A | 9/1997 | Cleveland et al. |
| 5,719,324 A | 2/1998 | Thundat et al. |
| 5,771,902 A | 6/1998 | Lee et al. |
| 5,781,331 A | 7/1998 | Carr et al. |
| 5,796,152 A | 8/1998 | Carr et al. |
| 5,810,325 A | 9/1998 | Carr |
| 5,811,017 A | 9/1998 | Matsuyama |
| 5,819,749 A | 10/1998 | Lee et al. |
| 5,908,981 A | 6/1999 | Atalar et al. |
| 5,918,263 A | 6/1999 | Thundat |
| 5,965,886 A | 10/1999 | Sauer et al. |
| 5,977,544 A | 11/1999 | Datskos et al. |
| 5,998,995 A | 12/1999 | Osiander et al. |
| 6,016,686 A | 1/2000 | Thundat |
| 6,041,642 A | 3/2000 | Duncan |
| 6,050,722 A | 4/2000 | Thundat et al. |
| 6,054,277 A | 4/2000 | Furcht et al. |
| 6,057,520 A | 5/2000 | Goodwin-Johansson |
| 6,096,559 A | 8/2000 | Thundat et al. |
| 6,118,124 A | 9/2000 | Thundat et al. |
| 6,130,464 A | 10/2000 | Carr |
| 6,167,748 B1 | 1/2001 | Britton, Jr. et al. |
| 6,181,131 B1 | 1/2001 | Bruland et al. |

(Continued)

OTHER PUBLICATIONS

T. Thundat, G. Chen, R. Warmack, D. Allison, and E. Wachter (1995) "Vapor detection using resonating microcantilevers" Analytical Chemistry 67, 519-521.

(Continued)

*Primary Examiner* — Sam P Siefke

(74) *Attorney, Agent, or Firm* — Steven M. Hoffberg; Ostrolenk Faber LLP

(57) ABSTRACT

A sensor, having a resonant frequency responsive to presence of an analyze, comprising a DC electrostatic excitation component, to produce a static force pulling a moveable element toward a backplate; an AC electrostatic excitation component, to produce an oscillation in the moveable element with respect to the backplate; and a sensor to detect contact between the moveable and the backplate.

25 Claims, 6 Drawing Sheets

U.S. PATENT DOCUMENTS

| | | |
|---|---|---|
| 6,189,374 B1 | 2/2001 | Adderton et al. |
| 6,212,939 B1 | 4/2001 | Thundat |
| 6,215,137 B1 | 4/2001 | Suzuki et al. |
| 6,229,683 B1 | 5/2001 | Goodwin-Johansson |
| 6,245,444 B1 | 6/2001 | Marcus et al. |
| 6,249,001 B1 | 6/2001 | Sauer et al. |
| 6,269,685 B1 | 8/2001 | Oden |
| 6,287,765 B1 | 9/2001 | Cubicciotti |
| 6,289,717 B1 | 9/2001 | Thundat et al. |
| 6,303,288 B1 | 10/2001 | Furcht et al. |
| 6,307,202 B1 | 10/2001 | Manalis et al. |
| 6,311,549 B1 | 11/2001 | Thundat et al. |
| 6,312,959 B1 | 11/2001 | Datskos |
| 6,325,904 B1 | 12/2001 | Peeters |
| 6,385,363 B1 | 5/2002 | Rajic et al. |
| 6,391,624 B1 | 5/2002 | Megerle |
| 6,392,233 B1 | 5/2002 | Channin et al. |
| 6,392,777 B1 | 5/2002 | Elliott et al. |
| 6,408,250 B1 | 6/2002 | Grate et al. |
| 6,444,972 B1 | 9/2002 | Datskos et al. |
| 6,471,136 B1 | 10/2002 | Chatterjee et al. |
| 6,523,392 B2 | 2/2003 | Porter et al. |
| 6,525,307 B1 | 2/2003 | Evans, III et al. |
| 6,530,266 B1 | 3/2003 | Adderton et al. |
| 6,545,276 B1 | 4/2003 | Sasaki |
| 6,583,416 B1 | 6/2003 | Villani |
| 6,605,039 B2 | 8/2003 | Houben et al. |
| 6,606,567 B2 | 8/2003 | Grate et al. |
| 6,628,392 B2 | 9/2003 | Kuroda et al. |
| 6,651,504 B1 | 11/2003 | Datskos |
| 6,668,627 B2 | 12/2003 | Lange et al. |
| 6,671,055 B1 | 12/2003 | Wavering et al. |
| 6,671,631 B2 | 12/2003 | Potyrailo et al. |
| 6,672,144 B2 | 1/2004 | Adderton et al. |
| 6,677,697 B2 | 1/2004 | Struckmeier et al. |
| 6,683,451 B1 | 1/2004 | Moore et al. |
| 6,762,025 B2 | 7/2004 | Cubicciotti |
| 6,762,056 B1 | 7/2004 | Peeters |
| 6,763,705 B1 | 7/2004 | Thundat et al. |
| 6,805,839 B2 | 10/2004 | Cunningham et al. |
| 6,810,720 B2 | 11/2004 | Adderton et al. |
| 6,818,959 B2 | 11/2004 | Montelius et al. |
| 6,823,717 B2 | 11/2004 | Porter et al. |
| 6,854,317 B2 | 2/2005 | Porter et al. |
| 6,860,939 B2 | 3/2005 | Hartzell |
| 6,864,692 B1 | 3/2005 | Patel et al. |
| 6,901,802 B2 | 6/2005 | Datskos |
| 6,906,339 B2 | 6/2005 | Dutta |
| 6,926,864 B2 | 8/2005 | Peeters et al. |
| 6,935,165 B2 | 8/2005 | Bashir et al. |
| 6,941,823 B1 | 9/2005 | Lai et al. |
| 6,943,448 B2 | 9/2005 | Gabriel et al. |
| 6,953,977 B2 | 10/2005 | Mlcak et al. |
| 6,972,423 B2 | 12/2005 | Welland et al. |
| 6,977,511 B2 | 12/2005 | Patel et al. |
| 6,989,235 B2 | 1/2006 | Chapsky et al. |
| 7,003,405 B1 | 2/2006 | Ho |
| 7,013,717 B1 | 3/2006 | Struckmeier et al. |
| 7,017,398 B2 | 3/2006 | Adderton et al. |
| 7,034,677 B2 | 4/2006 | Steinthal et al. |
| 7,036,357 B2 | 5/2006 | Adderton et al. |
| 7,044,007 B2 | 5/2006 | Struckmeier et al. |
| 7,044,911 B2 | 5/2006 | Drinan et al. |
| 7,055,378 B2 | 6/2006 | Su et al. |
| 7,064,834 B2 | 6/2006 | Johnson et al. |
| 7,067,104 B2 | 6/2006 | Sandhage |
| 7,086,288 B2 | 8/2006 | Lee et al. |
| 7,097,662 B2 | 8/2006 | Evans, III et al. |
| 7,105,301 B2 | 9/2006 | Su et al. |
| 7,105,358 B2 | 9/2006 | Majumdar et al. |
| 7,116,798 B1 | 10/2006 | Chawla |
| 7,125,451 B2 | 10/2006 | Hartzell |
| 7,128,783 B2 | 10/2006 | Hartzell |
| 7,135,070 B2 | 11/2006 | Hartzell |
| 7,141,210 B2 | 11/2006 | Bell et al. |
| 7,141,385 B2 | 11/2006 | Bottomley et al. |
| 7,148,803 B2 | 12/2006 | Bandy et al. |
| 7,153,702 B2 | 12/2006 | Lin et al. |
| 7,155,959 B2 | 1/2007 | Su et al. |
| 7,156,916 B2 | 1/2007 | Hartzell |
| 7,157,897 B2 | 1/2007 | Shekhawat et al. |
| 7,168,294 B2 | 1/2007 | Porter et al. |
| 7,171,312 B2 | 1/2007 | Steinthal et al. |
| 7,177,018 B2 | 2/2007 | Seeley |
| 7,179,421 B1 | 2/2007 | Ho |
| 7,184,200 B2 | 2/2007 | Dalakos et al. |
| 7,185,440 B2 | 3/2007 | Gage et al. |
| 2001/0020680 A1 | 9/2001 | Cunningham et al. |
| 2001/0028036 A1 | 10/2001 | Thundat et al. |
| 2001/0029774 A1 | 10/2001 | Grate et al. |
| 2002/0007667 A1 | 1/2002 | Pohl et al. |
| 2002/0010390 A1 | 1/2002 | Guice et al. |
| 2002/0034757 A1 | 3/2002 | Cubicciotti |
| 2002/0038083 A1 | 3/2002 | Houben et al. |
| 2002/0062684 A1 | 5/2002 | Adderton et al. |
| 2002/0092359 A1 | 7/2002 | Lange et al. |
| 2002/0102743 A1 | 8/2002 | Majumdar et al. |
| 2003/0004403 A1 | 1/2003 | Drinan et al. |
| 2003/0010097 A1 | 1/2003 | Porter et al. |
| 2003/0039693 A1 | 2/2003 | Sandhage |
| 2003/0047816 A1 | 3/2003 | Dutta |
| 2003/0054355 A1 | 3/2003 | Warthoe |
| 2003/0068655 A1 | 4/2003 | Bottomley et al. |
| 2003/0068657 A1 | 4/2003 | Lin et al. |
| 2003/0077660 A1 | 4/2003 | Pien et al. |
| 2003/0092016 A1 | 5/2003 | Wiggins et al. |
| 2003/0094036 A1 | 5/2003 | Adderton et al. |
| 2003/0099763 A1 | 5/2003 | Sandhage |
| 2003/0103262 A1 | 6/2003 | Descour et al. |
| 2003/0110844 A1 | 6/2003 | Struckmeier et al. |
| 2003/0113766 A1 | 6/2003 | Pepper et al. |
| 2003/0119220 A1 | 6/2003 | Mlcak et al. |
| 2003/0128361 A1 | 7/2003 | Kuroda et al. |
| 2003/0130804 A1 | 7/2003 | Potyrailo et al. |
| 2003/0186453 A1 | 10/2003 | Bell et al. |
| 2003/0186454 A1 | 10/2003 | Bruce et al. |
| 2003/0186455 A1 | 10/2003 | Bruce et al. |
| 2003/0197852 A1 | 10/2003 | Johnson et al. |
| 2003/0209058 A1 | 11/2003 | Merrill |
| 2003/0215844 A1 | 11/2003 | Chapsky et al. |
| 2003/0215865 A1 | 11/2003 | Mayer et al. |
| 2003/0222232 A1 | 12/2003 | Welland et al. |
| 2004/0007051 A1 | 1/2004 | Bashir et al. |
| 2004/0029108 A1 | 2/2004 | Bottomley et al. |
| 2004/0038426 A1 | 2/2004 | Manalis |
| 2004/0060358 A1 | 4/2004 | Datskos |
| 2004/0078219 A1 | 4/2004 | Kaylor et al. |
| 2004/0080319 A1 | 4/2004 | Merrill |
| 2004/0096357 A1 | 5/2004 | Majumdar et al. |
| 2004/0100376 A1 | 5/2004 | Lye et al. |
| 2004/0110161 A1 | 6/2004 | Kappel et al. |
| 2004/0115239 A1 | 6/2004 | Shastri et al. |
| 2004/0115711 A1 | 6/2004 | Su et al. |
| 2004/0132214 A1 | 7/2004 | Lin et al. |
| 2004/0152211 A1 | 8/2004 | Majumdar et al. |
| 2004/0165244 A1 | 8/2004 | Seeley |
| 2004/0194534 A1 | 10/2004 | Porter et al. |
| 2004/0194535 A1 | 10/2004 | Su et al. |
| 2004/0211243 A1 | 10/2004 | Porter et al. |
| 2004/0223881 A1 | 11/2004 | Cunningham et al. |
| 2004/0223884 A1 | 11/2004 | Chen et al. |
| 2004/0244488 A1 | 12/2004 | Tang et al. |
| 2004/0255651 A1 | 12/2004 | Adderton et al. |
| 2004/0262852 A1 | 12/2004 | Vafai et al. |
| 2005/0009197 A1 | 1/2005 | Adams et al. |
| 2005/0016921 A1 | 1/2005 | Gjerde et al. |
| 2005/0019941 A1 | 1/2005 | Gjerde et al. |
| 2005/0019950 A1 | 1/2005 | Gjerde et al. |
| 2005/0019951 A1 | 1/2005 | Gjerde et al. |
| 2005/0034512 A1 | 2/2005 | Su et al. |
| 2005/0043894 A1 | 2/2005 | Fernandez |
| 2005/0045543 A1 | 3/2005 | Gjerde et al. |
| 2005/0064581 A1 | 3/2005 | Manalis et al. |
| 2005/0066714 A1 | 3/2005 | Adderton et al. |
| 2005/0069461 A1 | 3/2005 | Thundat et al. |
| 2005/0074904 A1 | 4/2005 | Chin et al. |
| 2005/0081610 A1 | 4/2005 | Struckmeier et al. |

| | | |
|---|---|---|
| 2005/0088299 A1 | 4/2005 | Bandy et al. |
| 2005/0089890 A1 | 4/2005 | Cubicciotti |
| 2005/0101841 A9 | 5/2005 | Kaylor et al. |
| 2005/0106594 A1 | 5/2005 | Ellington et al. |
| 2005/0112621 A1 | 5/2005 | Kim et al. |
| 2005/0123563 A1 | 6/2005 | Doranz et al. |
| 2005/0151530 A1 | 7/2005 | Shekhawat et al. |
| 2005/0164285 A1 | 7/2005 | Patel et al. |
| 2005/0164299 A1 | 7/2005 | Stewart |
| 2005/0167172 A1 | 8/2005 | Fernandez |
| 2005/0167795 A1 | 8/2005 | Higashi |
| 2005/0176034 A1 | 8/2005 | Peeters et al. |
| 2005/0177223 A1 | 8/2005 | Palmaz |
| 2005/0195407 A1 | 9/2005 | Nordin et al. |
| 2005/0199047 A1 | 9/2005 | Adams et al. |
| 2005/0201963 A1 | 9/2005 | Dutta |
| 2005/0223806 A1 | 10/2005 | Thundat et al. |
| 2005/0227258 A1 | 10/2005 | Bright |
| 2005/0242339 A1 | 11/2005 | Beck |
| 2005/0244820 A1 | 11/2005 | Su et al. |
| 2005/0248454 A1 | 11/2005 | Hanson et al. |
| 2005/0248456 A1 | 11/2005 | Britton et al. |
| 2005/0255448 A1 | 11/2005 | Majumdar et al. |
| 2005/0255604 A1 | 11/2005 | Gjerde et al. |
| 2005/0265991 A1 | 12/2005 | Tuszynski et al. |
| 2005/0276726 A1 | 12/2005 | McGill et al. |
| 2006/0032289 A1 | 2/2006 | Pinnaduwage et al. |
| 2006/0033024 A1 | 2/2006 | Sparks et al. |
| 2006/0035234 A1 | 2/2006 | Henderson et al. |
| 2006/0047283 A1 | 3/2006 | Evans et al. |
| 2006/0053871 A1 | 3/2006 | Porter et al. |
| 2006/0057026 A1 | 3/2006 | Boiadjiev et al. |
| 2006/0058611 A1 | 3/2006 | Descour et al. |
| 2006/0059984 A1 | 3/2006 | Doktycz et al. |
| 2006/0062734 A1 | 3/2006 | Melker et al. |
| 2006/0071286 A1 | 4/2006 | Axelrod et al. |
| 2006/0072014 A1 | 4/2006 | Geng et al. |
| 2006/0078999 A1 | 4/2006 | Bell et al. |
| 2006/0118491 A1 | 6/2006 | Gjerde et al. |
| 2006/0121502 A1 | 6/2006 | Cain et al. |
| 2006/0123894 A1 | 6/2006 | Krause et al. |
| 2006/0124551 A1 | 6/2006 | Gjerde et al. |
| 2006/0131500 A1 | 6/2006 | Dalakos et al. |
| 2006/0133961 A1 | 6/2006 | Lim et al. |
| 2006/0135374 A1 | 6/2006 | Cooper et al. |
| 2006/0154248 A1 | 7/2006 | McGrew et al. |
| 2006/0160134 A1 | 7/2006 | Melker et al. |
| 2006/0174941 A1 | 8/2006 | Cohen et al. |
| 2006/0178841 A1 | 8/2006 | Fernandez |
| 2006/0181414 A1 | 8/2006 | Bandy et al. |
| 2006/0191320 A1 | 8/2006 | Pinnaduwage et al. |
| 2006/0191329 A1 | 8/2006 | Adderton et al. |
| 2006/0230817 A1 | 10/2006 | Schilowitz et al. |
| 2006/0253005 A1 | 11/2006 | Drinan et al. |
| 2006/0253259 A1 | 11/2006 | Fernandez |
| 2006/0255790 A1 | 11/2006 | Gaillard et al. |
| 2006/0257286 A1 | 11/2006 | Adams |
| 2006/0269861 A1 | 11/2006 | Hirano et al. |
| 2006/0272399 A1 | 12/2006 | Su et al. |
| 2006/0281077 A1 | 12/2006 | Lin et al. |
| 2006/0283240 A1 | 12/2006 | Struckmeier et al. |
| 2006/0283338 A1 | 12/2006 | Degertekin |
| 2006/0285685 A1 | 12/2006 | Msezane |
| 2007/0011899 A1 | 1/2007 | Gage et al. |
| 2007/0012094 A1 | 1/2007 | Degertekin et al. |
| 2007/0028668 A1 | 2/2007 | Goto et al. |
| 2007/0031832 A1 | 2/2007 | Watt et al. |
| 2007/0031944 A1 | 2/2007 | Leontis |
| 2007/0041142 A1 | 2/2007 | Lal et al. |
| 2007/0044545 A1 | 3/2007 | Beyder et al. |

OTHER PUBLICATIONS

E.A. Wachter, and T. Thundat (1995) "Micromechanical sensors for chemical and physical measurements" Rev. Sci. Instrum. 66, 3662-3667.

F. Battiston, J.-P. Ramseyer, H. Lang, M. Baller, C. Gerber, J. Gimzewski, E. Meyer and H. Guntherodt (2001) "A chemical sensor based on a microfabricated cantilever array with simultaneous resonance frequency and bending readout". Sensors and Actuators B 77, 122-131.

Y.M. Yang, H. Ji, and T. Thundat (2003) "Nerve agents detection using a Cu2+/L-cysteine bilayercoated microcantilever". Journal of the American Chemical Society 125, 1124-1125.

G.H. Wu, R. Datar, K. Hansen, T. Thundat, R. Cote, and A. Majumdar. (2001) "Bioassay of prostatespecific antigen (PSA) using microcantilevers". Nature Biotechnology 19, 856-860.

J.D. Adams, B. Rogers, L. Manning, M. Jones, T. Sulchek, K. Murray, B. Beneschott, Z. Hu, T. Thundat, H. Cavazos, and S.C. Minne (2003) "Piezoelectric self-sensing of adsorption-induced microcantilever bending". Appl. Phys. Lett., in press.

B. Rogers, L. Manning, M. Jones, T. Sulchek, K. Murray, B. Beneschott, J.D. Adams, Z. Hu and T. Thundat, H. Cavazos and S.C. Minne., Nov. 2003, "Mercury vapor detection with a selfsensing, resonating piezoelectric cantilever". Rev. Sci. Instrum.

L. A. Pinnaduwage, A. Gehl, D. L. Hedden, G. Muralidharan, T. Thundat, R.T. Lareau, T. Sulchek, L. Manning, B. Rogers, M. Jones, and J.D. Adams. (accepted 2003) "Detection of trinitrotoluene via deflagration on a microcantilever". Nature.

J.D. Adams, G. Parrott, C. Bauer, T. Sant, L. Manning, M. Jones, B. Rogers, D. McCorkle and T. L. Ferrell, Oct. 20, 2003, "Nanowatt chemical vapor detection with a self-sensing, piezoelectric microcantilever array". Appl. Phys. Lett.

Younis, et al., "Characterization of the Performance of Capacitive Switches activated by Mechanical Shock", J. Micromechanics and Microengineeering 17 (2007), 1360-1370.

Dohn et al., "Cantilever Based Mass Sensor With Hard Contact Readout", Applied Physics Letters, vol. 88, No. 264104, 2006. http://apl.aip.org.

Slava Krylov, et al, Parametric Excitation and Stabilization of Electrostatically Actuated Microstructures, Eccomas Thematic Conference on Computational Methods in Structural Dynamics and Earthquake Engineering, Jun. 13-16, 2007, Rethymno, Crete, Greece.

S. Chaterjee, et al, Nonlinear Dynamics of Electrostatically Actuated Microstructures Under the Effect of Squeeze Film Damping, Proceedings of the International Conference on Mechanical Engineering, 2009, Dec. 26-28, 2009, Dhaka, Bangladesh.

Changping Chen, et al, Nonlinear Dynamic Stability of an Electrically Actuated Microbeam Structure in Mems, Proceedings of the ASME 2011 International Mechanical Engineering Congress & Exposition, Nov. 11-17, 2011, Denver, Colorado.

Stefanie Gutschmidt, The Influence of Higher-Order Mode Shapes for Reduced-Order Models of Electrostatically Actuated Microbeams, Department of Mechanical Engineering, University of Canterbury, Christchurch, New Zealand.

JSNB Vamsee Gowtham A, Dynamic Analysis Ofelecrostatically Exited Micro Cantilever Beam, Department of Mechanical Engineering National Institute of Tehcnology-Rourkela, 2011.

Mohammad I. Younis, Response of Mems Devices Under Shock Loads, Proceedings of IMECE'05, 2005 ASME International Mechanical Engineering Congress and Exposition, Nov. 5-11, 2005, Orlando, Florida.

Veronique Rochus, et al, High Vibration Sensors: Modelling, Design and Integration, Aerospace & Mechanical Engineering, Department of University of Liege, Belgium.

S. Chaterjee, et al, Squeeze-Film Damping Characteristics of Cantilever Microresonators for Higher Modes of Flexural Vibration, International Journal of Engineering, Science and Technology, vol. 2, No. 4, 2010, pp. 187-199, Kolkata, India.

Andreu Fargas-Marques et al, Resonant Pull-In Condition in Parallel-Plate Elecrostatic Actuators, Journal of Microelectromechanical Systems, vol. 16, No. 5, Oct. 2007.

Michael G. Snow, Comprehensive Reduced-Order Models of Electrostatically Actuated Mems Switches and Their Dynamics Including Impact and Bounce, PRISM: NNSA Center for Prediction of Reliability, Integrity and Survivability of Microsystems, Aug. 15, 2010.

Raj K. Gupta, Electrostatic Pull-In Test Structure Design for In-Situ Mechanical Property Measurements of Microelectromechanical (MEMS), Massachusetts Institute of Technology, Jun. 1997.

M. Moghimi Zand, et al, Application of Homotopy Analysis Method in Studying Dynamic Pull-In Instability of Microsystems, Mechanics Research Communications 36 (2009) 851-858.

Raj K. Gupta, et al, Pull-In Time Dynamics as a Measure of Absolute Pressure, Microsystems Technologies Laboratories, Massachusetts Institute of Technology, Jan. 1997, Cambridge, MA.

Jeffrey F. Rhoads, et al, The Nonlinear Response of Resonant Microbeam Systems with Purely-Parametric Electrostatic Actuation, Journal of Micromechanics and Microengineering, 16 (2006) 890-899.

Y.M. Fu, et al, Nonlinear Static and Dynamic Responses of an Electrically Actuated Viscoelastic Microbeam, Acta Mech Sin, (2009), 25:211-218.

Wan-Chun Chuang, et al, Review on the Modeling of Electrostatic MEMS, Sensors 2010, 10, 6149-6171.

M. Moghimi Zand, et al, Contact Time Study of Electrostatically Actuated Microsystems, Transaction B: Mechanical Engineering, vol. 17, No. 5, 348-357.

R. C. Batra, et al, Vibrations of Narrow Microbeams Predeformed by an Electric Field, Journal of Sound and Vibration, 309 (2008), 600-612.

K. Das, et al, Symmetry Breaking, Snap-Through, and Pull-In Instabilities Under Dynamic Loading of Microelectromechanical Shallow Arches, Department of Engineering Science and Mechanics, Blacksburg, VA.

(a) Unactuated plate  (b) Actuated plate (a) Unactuated plate  (b) Actuated plate

RELIABLE SWITCH THAT IS TRIGGERED BY THE DETECTION OF A SPECIFIC GAS OR SUBSTANCE

RELATED APPLICATIONS

The present application claims benefit of priority from U.S. Provisional Patent Application Nos. 60/893,342 filed Mar. 6, 2007, and 60/943,303, filed Jun. 11, 2007, the entirety of which are expressly incorporated herein by reference.

FIELD OF THE INVENTION

The present invention relates to the field of microcantilever sensing devices.

BACKGROUND OF THE INVENTION

Microcantilevers that are properly functionalized with chemo- or bioselective coatings have been shown to be extremely sensitive to chemical and biological analytes in both vapor and liquid media. Microcantilevers therefore exhibit great promise as molecular and atomic recognition sensors for an extremely diverse set of applications including environmental monitoring, industrial process control, biological research, and homeland defense. Microcantilever operation is characterized by chemical reaction or adsorption of molecular species at the microcantilever surface which results in a change in the microcantelever's deflection and in properties such as its resonance frequency. While these induced changes can be very small (sub-nanometer cantilever deflection, for example), they are readily measurable with a laser beam reflection technique developed for atomic force microscope (AFM) cantilever measurements.

See:

Thundat, T., G. Chen, R. Warmack, D. Allison, and E. Wachter (1995) Vapor detection using resonating microcantilevers. Analytical Chemistry 67, 519-521.

Wachter, E. A. and T. Thundat (1995) Micromechanical sensors for chemical and physical measurements. Rev. Sci. Instrum. 66, 3662-3667.

Battiston, F., J.-P. Ramseyer, H. Lang, M. Baller, C. Gerber, J. Gimzewski, E. Meyer and H. Güntherodt (2001) "A chemical sensor based on a microfabricated cantilever array with simultaneous resonance frequency and bending readout". Sensors and Actuators B 77, 122-131.

Yang, Y. M., H. Ji, and T. Thundat (2003) "Nerve agents detection using a Cu2+/L-cysteine bilayercoated microcantilever". Journal of the American Chemical Society 125, 1124-1125.

Wu, G. H., R. Datar, K. Hansen, T. Thundat, R. Cote, and A. Majumdar. (2001) "Bioassay of prostatespecific antigen (PSA) using microcantilevers". Nature Biotechnology 19, 856-860.

J. D. Adams, B. Rogers, L. Manning, M. Jones, T. Sulchek, K. Murray, B. Beneschott, Z. Hu, T. Thundat, H. Cavazos, and S. C. Minne (2003) "Piezoelectric self-sensing of adsorption-induced microcantilever bending". Appl. Phys. Lett., in press B. Rogers, L. Manning, M. Jones, T. Sulchek, K. Murray, B. Beneschott, J. D. Adams, Z. Hu and T. Thundat, H. Cavazos and S. C. Minne. (to be published November 2003) "Mercury vapor detection with a selfsensing, resonating piezoelectric cantilever". Rev. Sci. Instrum.

L. A. Pinnaduwage, A. Gehl, D. L. Hedden, G. Muralidharan, T. Thundat, R. T. Lareau, T. Sulchek, L. Manning, B. Rogers, M. Jones, and J. D. Adams. (accepted 2003) "Detection of trinitrotoluene via deflagration on a microcantilever". Nature J. D. Adams, G. Parrott, C. Bauer, T. Sant, L. Manning, M. Jones, B. Rogers, D. McCorkle and T. L. Ferrell. (to be published Oct. 20, 2003) "Nanowatt chemical vapor detection with a self-sensing, piezoelectric microcantilever array". Appl. Phys. Lett.

J. English, Y. Shtessel, M. Yegnaraman and M. George, "MEMS Device Modeling Microcantilever Sensor via Second Order Sliding Mode Control", Nanotech 2006 Vol. 3, Technical Proceedings of the 2006 NSTI Nanotechnology Conference and Trade Show, Volume 3, Chapter 6.

| | |
|---|---|
| 7,185,440 | Sensing contact probe |
| 7,184,200 | Passive broadband infrared optical limiter device based on a micro-optomechanical cantilever array |
| 7,179,421 | Multi-pin chemiresistors for microchemical sensors |
| 7,177,018 | Multiplex illuminator and device reader for microcantilever array |
| 7,171,312 | Chemical and biological agent sensor array detectors |
| 7,168,294 | Embedded piezoelectric microcantilever sensors |
| 7,157,897 | Method and system for electronic detection of mechanical perturbations using BIMOS readouts |
| 7,156,916 | Monolithic integrated crystal-structure-processed mechanical, and combined mechanical and electrical devices, and methods and systems for making |
| 7,155,959 | Nanodisk sensor and sensor array |
| 7,153,702 | Label-free methods for performing assays using a colorimetric resonant reflectance optical biosensor |
| 7,148,803 | Radio frequency identification (RFID) based sensor networks |
| 7,141,385 | Microcantilever apparatus and methods for detection of enzymes, enzyme substrates, and enzyme effectors |
| 7,141,210 | Apparatus and method for a nanocalorimeter for detecting chemical reactions |
| 7,135,070 | Monolithic stacked/layered crystal-structure-processed mechanical, and combined mechanical and electrical, devices and methods and systems for making |
| 7,128,783 | Thin-film crystal-structure-processed mechanical devices, and methods and systems for making |
| 7,125,451 | Crystal-structure-processed mechanical devices and methods and systems for making |
| 7,116,798 | Fare card explosive detection system and process |
| 7,105,358 | Apparatus and method for visually identifying microforces with a palette of cantilever array blocks |
| 7,105,301 | Detecting molecular binding by monitoring feedback controlled cantilever deflections |
| 7,097,662 | In-vivo orthopedic implant diagnostic device for sensing load, wear, and infection |
| 7,086,288 | Thin membrane transducer |
| 7,067,104 | Shaped microcomponent via reactive conversion of biologically-derived microtemplates |
| 7,064,834 | Method for analyzing impurities in carbon dioxide |
| 7,055,378 | System for wide frequency dynamic nanomechanical analysis |
| 7,044,911 | Gateway platform for biological monitoring and delivery of therapeutic compounds |
| 7,044,007 | Force scanning probe microscope |
| 7,036,357 | Dynamic activation for an atomic force microscope and method of use thereof |
| 7,034,677 | Non-specific sensor array detectors |
| 7,017,398 | Active probe for an atomic force microscope and method for use thereof |
| 7,013,717 | Manual control with force-feedback for probe microscopy-based force spectroscopy |
| 7,003,405 | Methods for characterizing subsurface volatile contaminants using in-situ sensors |
| 6,989,235 | Single molecule detection of bio-agents using the F1-ATPase biomolecular motor |
| 6,977,511 | Sensor and sensor array having improved selectivity |
| 6,972,423 | Sensor |
| 6,953,977 | Micromechanical piezoelectric device |
| 6,943,448 | Multi-metal layer MEMS structure and process for making the same |

-continued

| | |
|---|---|
| 6,941,823 | Apparatus and method to compensate for stress in a microcantilever |
| 6,935,165 | Microscale sensor element and related device and method of use |
| 6,926,864 | Microfluidics apparatus and methods for use thereof |
| 6,906,339 | Passivated nanoparticles, method of fabrication thereof, and devices incorporating nanoparticles |
| 6,901,802 | Acoustic sensors using microstructures tunable with energy other than acoustic energy |
| 6,864,692 | Sensor having improved selectivity |
| 6,860,939 | Semiconductor crystal-structure-processed mechanical devices, and methods and systems for making |
| 6,854,317 | Embedded piezoelectric microcantilever sensors |
| 6,823,717 | Hybrid microcantilever sensors |
| 6,818,959 | MEMS devices with voltage driven flexible elements |
| 6,810,720 | Active probe for an atomic force microscope and method of use thereof |
| 6,805,839 | Response microcantilever thermal detector |
| 6,763,705 | High throughput microcantilever detector |
| 6,762,056 | Rapid method for determining potential binding sites of a protein |
| 6,762,025 | Single-molecule selection methods and compositions therefrom |
| 6,683,451 | Magnetic resonance force microscope for the study of biological systems |
| 6,677,697 | Force scanning probe microscope |
| 6,672,144 | Dynamic activation for an atomic force microscope and method of use thereof |
| 6,671,631 | Systems and methods for analyzing viscoelastic properties of combinatorial libraries of materials |
| 6,671,055 | Interferometric sensors utilizing bulk sensing mediums extrinsic to the input/output optical fiber |
| 6,668,627 | Sensor apparatus with magnetically deflected cantilever |
| 6,651,504 | Acoustic sensors using microstructures tunable with energy other than acoustic energy |
| 6,628,392 | Light modulation apparatus and optical switch, movement detecting device and distance measuring device, alignment device and semiconductor aligner, and processes thereof |
| 6,606,567 | Methods for characterizing, classifying, and identifying unknowns in samples |
| 6,605,039 | Cell-based biosensors suitable for implantable medical device applications |
| 6,583,416 | Uncooled IR detector array having improved temperature stability and reduced fixed pattern noise |
| 6,545,276 | Near field optical microscope |
| 6,530,266 | Active probe for an atomic force microscope and method of use thereof |
| 6,525,307 | Integrated optical interrogation of micro-structures |
| 6,523,392 | Microcantilever sensor |
| 6,471,136 | Biosensors for monitoring air conditioning and refrigeration processes |
| 6,444,972 | Apparatus and method for detecting electromagnetic radiation using electron photoemission in a micro-mechanical sensor |
| 6,408,250 | Methods for characterizing, classifying, and identifying unknowns in samples |
| 6,392,777 | Opto-mechanical device |
| 6,392,233 | Optomechanical radiant energy detector |
| 6,391,624 | Highly sensitive biological agent probe |
| 6,385,363 | Photo-induced micro-mechanical optical switch |
| 6,325,904 | Nanoelectrode arrays |
| 6,312,959 | Method using photo-induced and thermal bending of MEMS sensors |
| 6,311,549 | Micromechanical transient sensor for measuring viscosity and density of a fluid |
| 6,307,202 | Bimorph spirals for uncooled photothermal spectroscopy |
| 6,303,288 | Integrated microchip genetic testing system |
| 6,289,717 | Micromechanical antibody sensor |
| 6,287,765 | Methods for detecting and identifying single molecules |
| 6,269,685 | Viscosity measuring using microcantilevers |
| 6,249,001 | Infrared imager using room temperature capacitance sensor |
| 6,245,444 | Micromachined element and method of fabrication thereof |
| 6,229,683 | High voltage micromachined electrostatic switch |
| 6,215,137 | Micromechanical sensor for scanning thermal imaging microscope and method of making the same |
| 6,212,939 | Uncoated microcantilevers as chemical sensors |
| 6,189,374 | Active probe for an atomic force microscope and method of use thereof |
| 6,181,131 | Magnetic resonance force microscopy with oscillator actuation |
| 6,167,748 | Capacitively readout multi-element sensor array with common-mode cancellation |
| 6,130,464 | Latching microaccelerometer |
| 6,118,124 | Electromagnetic and nuclear radiation detector using micromechanical sensors |
| 6,096,559 | Micromechanical calorimetric sensor |
| 6,057,520 | Arc resistant high voltage micromachined electrostatic switch |
| 6,054,277 | Integrated microchip genetic testing system |
| 6,050,722 | Non-contact passive temperature measuring system and method of operation using micro-mechanical sensors |
| 6,041,642 | Method and apparatus for sensing the natural frequency of a cantilevered body |
| 6,016,686 | Micromechanical potentiometric sensors |
| 5,998,995 | Microelectromechanical (MEMS)-based magneto strictive magnetometer |
| 5,977,544 | Uncooled infrared photon detector and multicolor infrared detection using microoptomechanical sensors |
| 5,965,886 | Infrared imager using room temperature capacitance sensor |
| 5,918,263 | Microcantilever detector for explosives |
| 5,908,981 | Interdigital deflection sensor for microcantilevers |
| 5,819,749 | Microvalve |
| 5,811,017 | Cantilever for use in a scanning probe microscope and method of manufacturing the same |
| 5,810,325 | Microvalve |
| 5,796,152 | Cantilevered microstructure |
| 5,781,331 | Optical micro shutter array |
| 5,771,902 | Micromachined actuators/sensors for intratubular positioning/steering |
| 5,719,324 | Microcantilever sensor |
| 5,670,712 | Method and apparatus for magnetic force control of a scanning probe |
| 5,663,507 | Semiconductor piezoelectric strain measuring transducer |
| 5,580,827 | Casting sharpened microminiature tips |
| 5,455,419 | Micromechanical sensor and sensor fabrication process |
| 5,445,008 | Microbar sensor |
| 5,282,924 | Micromechanical sensor fabrication process |
| 5,272,913 | Cantilever for a scanning probe microscope and a method of manufacturing the same |
| 5,171,992 | Nanometer scale probe for an atomic force microscope, and method for making same |
| 5,116,462 | Method of producing micromechanical sensors for the AFM/STM profilometry |
| 5,051,379 | Method of producing micromechanical sensors for the AFM/STM profilometry and micromechanical AFM/STM sensor head |
| 20070044545 | Oscillator and method of making for atomic force microscope and other applications |
| 20070041142 | Relay-connected semiconductor transistors |
| 20070031944 | RNA complexes, methods of their production |
| 20070031832 | Methods of constructing biodiverse gene fragment libraries and biological modulators isolated therefrom |
| 20070028668 | MOLECULE DETECTION SENSOR, DETECTION SENSOR, AND GAS TRANSFERRING PUMP |
| 20070012094 | Integrated displacement sensors for probe microscopy and force spectroscopy |
| 20070011899 | SENSING CONTACT PROBE |
| 20060285685 | DNA Based Identification and Tracking System |
| 20060283338 | Force sensing integrated readout and active tip based probe microscope systems |
| 20060283240 | FORCE SCANNING PROBE MICROSCOPE |
| 20060281077 | Label-free methods for performing assays using a colorimetric resonant reflectance optical biosensor |
| 20060272399 | System for wide frequency dynamic nanomechanical analysis |
| 20060269861 | Manufacturing method of electrostatic charge image developing toner, and electrostatic charge image developing toner |
| 20060257286 | Self-sensing array of microcantilevers for chemical detection |
| 20060255790 | Method and apparatus for detecting resonance in electrostatically driven elements |
| 20060253259 | Integrated biosensor and simulation system for diagnosis and therapy |

| | -continued | | | -continued |
|---|---|---|---|---|
| 20060253005 | Gateway platform for biological monitoring and delivery of therapeutic compounds | | 20050112621 | Quantitative biopolymer detecting system using monolithic piezoelectric cantilever by resonant frequency shift, method for fabricating the same system and method for detecting biopolymer quantitatively using the same system |
| 20060230817 | Microcantilever stress sensor for fluid analysis | | | |
| 20060191329 | Dynamic activation for an atomic force microscope and method of use thereof | | | |
| 20060191320 | Chemically-functionalized microcantilevers for detection of chemical, biological and explosive material | | 20050106594 | In vitro selection of aptamer beacons |
| | | | 20050101841 | Healthcare networks with biosensors |
| | | | 20050089890 | Multimolecular devices and drug delivery systems |
| 20060181414 | Radio frequency identification (RFID) based sensor networks | | 20050088299 | Radio frequency identification (RFID) based sensor networks |
| 20060178841 | Integrated biosensor and simulation system for diagnosis and therapy | | 20050081610 | Force scanning probe microscope |
| | | | 20050074904 | Magnetostrictive ligand sensor |
| 20060174941 | In-line gas purity monitoring and control system | | 20050069461 | Multi-purpose multi-function surface-tension microfluidic manipulator |
| 20060160134 | Novel application of biosensors for diagnosis and treatment of disease | | 20050066714 | Active probe for an atomic force microscope and method for use thereof |
| 20060154248 | Manufacturing method and readout system for biopolymer arrays | | 20050064581 | Fabrication and packaging of suspended microchannel detectors |
| 20060135374 | Indicating lubricant additive | | | |
| 20060133961 | Bi-material cantilevers with flipped over material sections and structures formed therefrom | | 20050045543 | Method and device for extracting an analyte |
| | | | 20050043894 | Integrated biosensor and simulation system for diagnosis and therapy |
| 20060131500 | Passive broadband infrared optical limiter device based on a microoptomechanical cantilever array | | 20050034512 | System for wide frequency dynamic nanomechanical analysis |
| 20060124551 | Method and device for sample preparation | | 20050019951 | Method and device for extracting an analyte |
| 20060123894 | SPM sensor | | 20050019950 | Method and device for extracting an analyte |
| 20060121502 | Microfluidics apparatus for cantilevers and methods of use therefor | | 20050019941 | Method and device for extracting an analyte |
| | | | 20050016921 | Method and device for extracting an analyte |
| 20060118491 | Method and device for desalting an analyte | | 20050009197 | Chemical sensor with oscillating cantilevered probe and mechanical stop |
| 20060078999 | Apparatus and method for a nanocalorimeter for detecting chemical reactions | | | |
| | | | 20040262852 | Methods and devices comprising flexible seals for modulating or controlling flow and heat |
| 20060072014 | Smart optical sensor (SOS) hardware and software platform | | 20040255651 | Dynamic activation for an atomic force microscope and method of use thereof |
| 20060071286 | Polymeric piezoresistive sensors | | | |
| 20060062734 | Methods and systems for preventing diversion of prescription drugs | | 20040244488 | On-chip magnetic force actuation of microcantilevers by coplanar coils |
| 20060059984 | Coupled spring system for measuring molecular forces | | 20040223884 | Chemical sensor responsive to change in volume of material exposed to target particle |
| 20060058611 | Multimodal miniature microscope | | | |
| 20060057026 | Gold thiolate and photochemically functionalized microcantilevers using molecular recognition agents | | 20040223881 | Detection of biochemical interactions on a biosensor using tunable filters and tunable lasers |
| 20060053871 | Embedded piezoelectric microcantilever sensors | | 20040211243 | EMBEDDED PIEZOELECTRIC MICROCANTILEVER SENSORS |
| 20060047283 | In-vivo orthopedic implant diagnostic device for sensing load, wear, and infection | | | |
| | | | 20040194535 | Nanodisk sensor and sensor array |
| 20060035234 | Method and apparatus for molecular analysis in small sample volumes | | 20040194534 | HYBRID MICROCANTILEVER SENSORS |
| | | | 20040165244 | Multiplex illuminator and device reader for micro-cantilever array |
| 20060033024 | Scanning probe microscopy with inherent disturbance suppression | | | |
| | | | 20040152211 | System and method for multiplexed biomolecular analysis |
| 20060032289 | Non-optical explosive sensor based on two-track piezoresistive microcantilever | | 20040132214 | Label-free methods for performing assays using a colorimetric resonant optical biosensor |
| 20050276726 | Microelectro-mechanical chemical sensor | | | |
| 20050265991 | Drug delivery apparatus utilizing cantilever | | 20040115711 | Detecting molecular binding by monitoring feedback controlled cantilever deflections |
| 20050255604 | Method and device for extracting an analyte | | | |
| 20050255448 | System for amplifying optical detection of cantilever deflection | | 20040115239 | Engineering of material surfaces |
| | | | 20040110161 | Method for detecting mutations in nucleotide sequences |
| 20050248456 | Space charge dosimeters for extremely low power measurements of radiation in shipping containers | | 20040100376 | Healthcare monitoring system |
| | | | 20040096357 | Composite sensor membrane |
| 20050248454 | Marine asset security and tracking (MAST) system | | 20040080319 | MIP microcantilever sensor and a method of using thereof |
| 20050244820 | Detecting molecular binding by monitoring feedback controlled cantilever deflections | | 20040078219 | Healthcare networks with biosensors |
| | | | 20040060358 | Acoustic sensors using microstructures tunable with energy other than acoustic energy |
| 20050242339 | Apparatus and method for transverse characterization of materials | | | |
| | | | 20040038426 | Measurement of concentrations and binding energetics |
| 20050227258 | Site selectively tagged and templated molecularly imprinted polymers for sensor applications | | 20040029108 | Microcantilever apparatus and methods for detection of enzymes, enzyme substrates, and enzyme effectors |
| 20050223806 | Surface wave chemical detector using optical radiation | | 20040007051 | Microscale sensor element and related device and method of manufacture |
| 20050201963 | Passivated nanoparticles, method of fabrication thereof, and devices incorporating nanoparticles | | | |
| | | | 20030222232 | Sensor |
| 20050199047 | Liquid cell and passivated probe for atomic force microscopy and chemical sensing | | 20030215865 | Integrated nanomechanical sensor array chips |
| | | | 20030215844 | Single molecule detection of bio-agents using the F1-ATPase biomolecular motor |
| 20050195407 | Optical waveguide microcantilever with differential output and associated methods of cantilever sensing | | 20030209058 | MIP microcantilever sensor and a method of using thereof |
| | | | 20030197852 | Method for analyzing impurities in carbon dioxide |
| 20050177223 | Medical devices having MEMs functionality and methods of making same | | 20030186455 | Apparatus and method for multiple target assay for drug discovery |
| 20050176034 | Microfluidics apparatus and methods of use therefor | | | |
| 20050167795 | Electronic devices and its production methods | | 20030186454 | Apparatus and method for lead profiling assay |
| 20050167172 | Telematic method and apparatus with integrated power source | | 20030186453 | Apparatus and method for a nanocalorimeter for detecting chemical reactions |
| 20050164299 | Phase change sensor | | 20030130804 | Systems and methods for analyzing viscoelastic properties of combinatorial libraries of materials |
| 20050164285 | Sensor and sensor array having improved selectivity | | | |
| 20050151530 | Method and system for electronic detection of mechanical perturbations using BiMOS readouts | | 20030128361 | LIGHT MODULATION APPARATUS AND OPTICAL SWITCH, MOVEMENT DETECTING DEVICE AND DISTANCE MEASURING DEVICE, ALIGNMENT DEVICE AND SEMICONDUCTOR ALIGNER, AND PROCESSES THEREOF |
| 20050123563 | Lipoparticles comprising proteins, methods of making, and using the same | | | |

| | |
|---|---|
| 20030119220 | Micromechanical piezoelectric device |
| 20030113766 | Amine activated colorimetric resonant biosensor |
| 20030110844 | Force scanning probe microscope |
| 20030103262 | Multimodal miniature microscope |
| 20030099763 | Shaped microcomponent via reactive conversion of biologically-derived microtemplates |
| 20030094036 | Active probe for an atomic force microscope and method of use thereof |
| 20030092016 | Microfluidics apparatus and methods for use thereof |
| 20030077660 | Method and apparatus for biosensor spectral shift detection |
| 20030068657 | Label-free methods for performing assays using a colorimetric resonant reflectance optical biosensor |
| 20030068655 | Microcantilever apparatus and methods for detection of enzymes |
| 20030054355 | Microsensors and method for detecting target analytes |
| 20030047816 | Passivated nanoparticles, method of fabrication thereof, and devices incorporating nanoparticles |
| 20030039693 | Shaped microcomponents via reactive conversion of biologically-derived microtemplates |
| 20030010097 | MICROCANTILEVER SENSOR |
| 20030004403 | Gateway platform for biological monitoring and delivery of therapeutic compounds |
| 20020102743 | Apparatus and method for visually identifying micro-forces with a palette of cantilever array blocks |
| 20020092359 | Sensor apparatus and cantilever for it |
| 20020062684 | Dynamic activation for an atomic force microscope and method of use thereof |
| 20020038083 | Cell-based biosensors suitable for implantable medical device applications |
| 20020034757 | Single-molecule selection methods and compositions therefrom |
| 20020010390 | Method and system for monitoring the health and status of livestock and other animals |
| 20020007667 | Method and apparatus for the controlled conditioning of scanning probes |
| 20010029774 | Methods for characterizing, classifying, and identifying unknowns in samples |
| 20010028036 | Wavelength dispersive infrared detector and micro spectrometer using microcantilevers |
| 20010020680 | Response microcantilever thermal detector |
| 20040078219 | Healthcare networks with biosensors |
| 20040060358 | Acoustic sensors using microstructures tunable with energy other than acoustic energy |
| 20040038426 | Measurement of concentrations and binding energetics |
| 20040029108 | Microcantilever apparatus and methods for detection of enzymes, enzyme substrates, and enzyme effectors |
| 20040007051 | Microscale sensor element and related device and method of manufacture |
| 20030222232 | Sensor |
| 20030215865 | Integrated nanomechanical sensor array chips |
| 20030215844 | Single molecule detection of bio-agents using the F1-ATPase biomolecular motor |
| 20030209058 | MIP microcantilever sensor and a method of using thereof |
| 20030197852 | Method for analyzing impurities in carbon dioxide |
| 20030186455 | Apparatus and method for multiple target assay for drug discovery |
| 20030186454 | Apparatus and method for lead profiling assay |
| 20030186453 | Apparatus and method for a nanocalorimeter for detecting chemical reactions |
| 20030130804 | Systems and methods for analyzing viscoelastic properties of combinatorial libraries of materials |
| 20030128361 | LIGHT MODULATION APPARATUS AND OPTICAL SWITCH, MOVEMENT DETECTING DEVICE AND DISTANCE MEASURING DEVICE, ALIGNMENT DEVICE AND SEMICONDUCTOR ALIGNER, AND PROCESSES THEREOF |
| 20030119220 | Micromechanical piezoelectric device |
| 20030113766 | Amine activated colorimetric resonant biosensor |
| 20030110844 | Force scanning probe microscope |
| 20030103262 | Multimodal miniature microscope |
| 20030099763 | Shaped microcomponent via reactive conversion of biologically-derived microtemplates |
| 20030094036 | Active probe for an atomic force microscope and method of use thereof |
| 20030092016 | Microfluidics apparatus and methods for use thereof |
| 20030077660 | Method and apparatus for biosensor spectral shift detection |
| 20030068657 | Label-free methods for performing assays using a colorimetric resonant reflectance optical biosensor |
| 20030068655 | Microcantilever apparatus and methods for detection of enzymes |
| 20030054355 | Microsensors and method for detecting target analytes |
| 20030047816 | Passivated nanoparticles, method of fabrication thereof, and devices incorporating nanoparticles |
| 20030039693 | Shaped microcomponents via reactive conversion of biologically-derived microtemplates |
| 20030010097 | MICROCANTILEVER SENSOR |
| 20030004403 | Gateway platform for biological monitoring and delivery of therapeutic compounds |
| 20020102743 | Apparatus and method for visually identifying micro-forces with a palette of cantilever array blocks |
| 20020092359 | Sensor apparatus and cantilever for it |
| 20020062684 | Dynamic activation for an atomic force microscope and method of use thereof |
| 20020038083 | Cell-based biosensors suitable for implantable medical device applications |
| 20020034757 | Single-molecule selection methods and compositions therefrom |
| 20020010390 | Method and system for monitoring the health and status of livestock and other animals |
| 20020007667 | Method and apparatus for the controlled conditioning of scanning probes |
| 20010029774 | Methods for characterizing, classifying, and identifying unknowns in samples |
| 20010028036 | Wavelength dispersive infrared detector and micro spectrometer using microcantilevers |
| 20010020680 | Response microcantilever thermal detector |

Each of the above references is expressly incorporated herein by reference.

SUMMARY OF THE INVENTION

The present invention provides a resonant mechanical structure which is forced to escape from a potential well; in this case the potential well is electrostatic. This escape leads to dynamic pull-in and collapse of the structure. According to a preferred embodiment, the collapse results in a switching action of an electrical circuit.

While a preferred embodiment of the invention excites the resonant mechanical structure with an alternating electric field (AC) while simultaneously biasing it with a static electric field component (DC), the structure can be driven near its natural frequency (resonance) by any excitation method, for example, with a piezoelectric effect, an electromagnetic or magnetic effect, a thermal effect, a photoresponse effect, and acoustic methods.

An embodiment of the present invention combines the functions of two devices: a sensor (e.g., gas or solute) and an electro-mechanical switch. This device is capable of detecting a specific kind of gas or substance, such as an explosive gas, and then sends a strong electrical signal (e.g., low impedance output) as a sign or indication of this detection. This signal can be used to actuate an alarming system or to activate a defensive or a security system.

The present state of the art has many examples of gas sensors that can detect specific gases, but the signal obtained from this detection is not strong enough or usable to be utilized to do an action. In order to utilize the obtained signal from such devices, a complex system of sensors, actuators, decision units, amplifiers, analogue-to digital converters, and other electronic components, is needed. These may be expensive and complex and may not be reliable enough. If any of those single components becomes non-functional, the whole system fails. The new device, on the other hand, is reliable, simple, relatively less expensive, and can be made to be of high sensitivity.

An embodiment according to the present invention has high reliability. When configured as a switch, it will operate only when the concentration of the hazardous gas or material exceeds the permitted percentage, then it will send a direct electrical signal. So if there is no risk, no signal comes out; if there is any danger, there will be a signal. In some cases, it may operate in inverse as a "normally closed" output, wherein the hazardous condition is signified by an interruption of the signal. An integration of multiple sensing elements is possible, sensing the same or different effects at various sensitivities and thresholds, and it is also possible to provide a differential output in which one switch is closed and another opened to indicate the condition.

A sensor device according to various embodiments of the invention is simple to fabricate: for example, it may consist of only a microbeam capacitor with an appropriate coating, and a conductive path sensor. Such a device is typically excited with a DC potential to provide a pull in force, and an AC signal to generate an oscillation.

The present invention is not limited to functioning as an actuator, and thus can also function as a sensor having an analog and/or proportional output. In that case, a circuit is provided to analyze a characteristic of the oscillating element, such as its position, oscillation amplitude, resonance frequency or non-linearities in transfer function, to determine an amount or change in response of the sensor to the condition being sensed. It is noted that calibration of the sensor and/or switch may be achieved by altering the AC and/or DC voltages.

The sensor may also be made responsive to external mechanical influences, such as shock or inertia. See, Younis et al., "Characterization of the Performance of Capacitive Switches activated by Mechanical Shock", *J. Micromechanics and Microengineeering* 17 (2007), 1360-1370, expressly incorporated herein by reference.

The present invention has all the advantages of the MEMS sensors and actuators (low power consumption, low weight, etc.). The principals involved may also apply to nano-electromechanical sensors, formed, for example, with nanotubes, and may be scaled to larger sizes as well. Thus, while the MEMS technology is not a size or scale limitation of the invention, though devices and features obtained through application of masking, etching and/or selective oxidation of silicon wafers are presently preferred.

BRIEF DESCRIPTION OF THE DRAWINGS

A complete understanding of the present invention may be obtained by reference to the accompanying drawings, when considered in conjunction with the subsequent detailed description, in which.

DETAILED DESCRIPTION OF THE PREFERRED EMBODIMENTS

Figure 1:
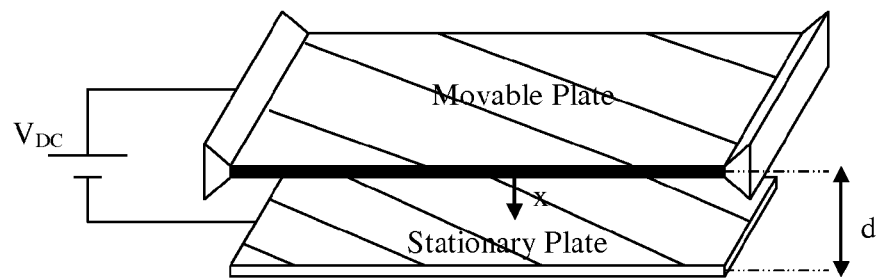
FIG. 1 shows a parallel-plate capacitor.

The present invention relies on electrostatic actuation of a parallel plate capacitor, shown in FIG. 1, in which one plate (or any other structure of arbitrary shape) is stationary and the other plate is movable and is actuated or biased by an electrostatic DC force. Indeed, the existence of a stationary plate is not required, though it provides a simplified construction and analysis thereof.

Figure 2:
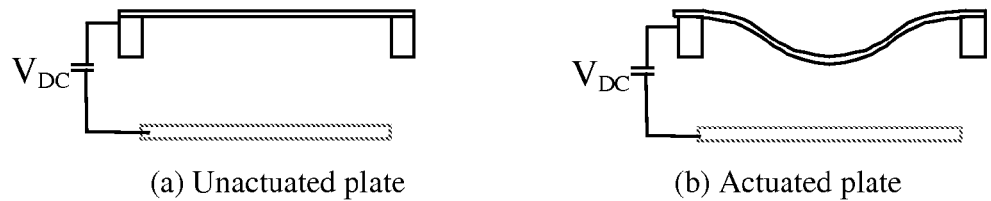
FIGS. 2 and 3 show a parallel plate capacitor before (a) and after (b) the application of a small and large DC voltage, respectively, producing a static force.

The DC force deflects the moveable plate toward the other stationary plate (FIG. 2b). If the electrostatic force is small, the moveable plate is maintained in a deflected position, at which the elastic restoring force of the plate is in equilibrium with the opposing electrostatic force.

Figure 3:
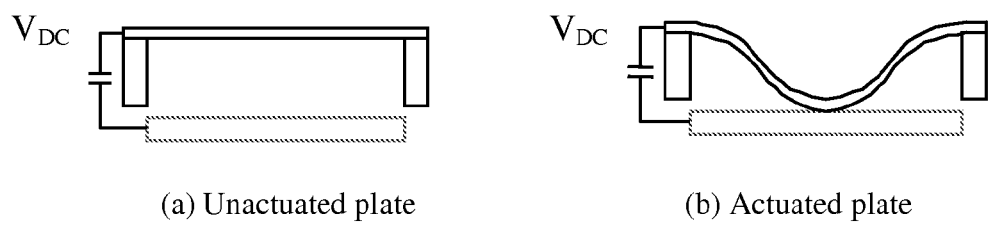
Figure 4:
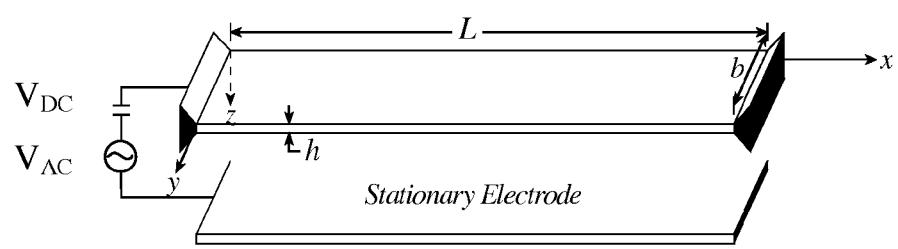
FIG. 4 shows a parallel plate capacitor showing the excitation using both a DC load and an AC harmonic load.

When the DC voltage increases, the electrostatic force increases, and hence the plate deflection increases. There is an upper limit for the DC voltage, beyond which the mechanical restoring force of the plate can no longer resist the opposing electrostatic force. This leads to a "collapse" of the plate, which hits the stationary plate (FIG. 3b). This structural instability phenomenon is known as pull-in. In accordance with an embodiment of the invention, the contact of the two plates provides a switching function, which is potentially relatively low impedance, and thus can provide direct drive capability, without requiring an electronic sensing circuit or amplifier in order to provide a suitable signal for external use.

Pull-in can also occur due to the actuation of a combination of a DC load and an AC harmonic load. The DC load deflects the movable electrode slightly and the AC load vibrates the electrode around the new deflected position. Because pull-in here occurs due to a dynamic (harmonic) loading, it is called dynamic pull-in, as opposed to static pull-in, which occurs due the actuation of DC loading only, as explain above with respect to FIGS. 2 and 3.

The AC harmonic load has the form of $v(t)=V_{AC}\cos(\Omega t)$, where $V_{AC}$ is the amplitude of the AC excitation and $\Omega$ is the excitation frequency. The maximum influence of this excitation on the movable structure (electrode) occurs when the excitation frequency $\Omega$ gets close to the natural frequency of the structure $\omega_{natural}$. This causes a resonant behavior. Hence, we expect the dynamic pull-in phenomenon to occur in the range of excitation frequency that is close to the natural frequency of the movable electrode.

To demonstrate an example of the invention, we consider a parallel plate capacitor employing a cantilever beam as its upper electrode. The microbeam is made of silicon, with length 100 microns, width 10 microns, and thickness 0.1 micron. The gap spacing between the beam the substrate (the lower stationary electrode) is d=2 microns. The quality factor of the microbeam is assumed to be 10. The natural frequency of this microbeam is equal $3.5*\omega_{nat}$, where $\omega_{nat}$ is a universal natural frequency for beams. So $\omega_{natural}/\omega_{nat}=3.5$. When the beam is biased by $V_{DC}=0.4$ V, $\omega_{natural}/\omega_{nat}$ drops to 3.3.

Figure 5:
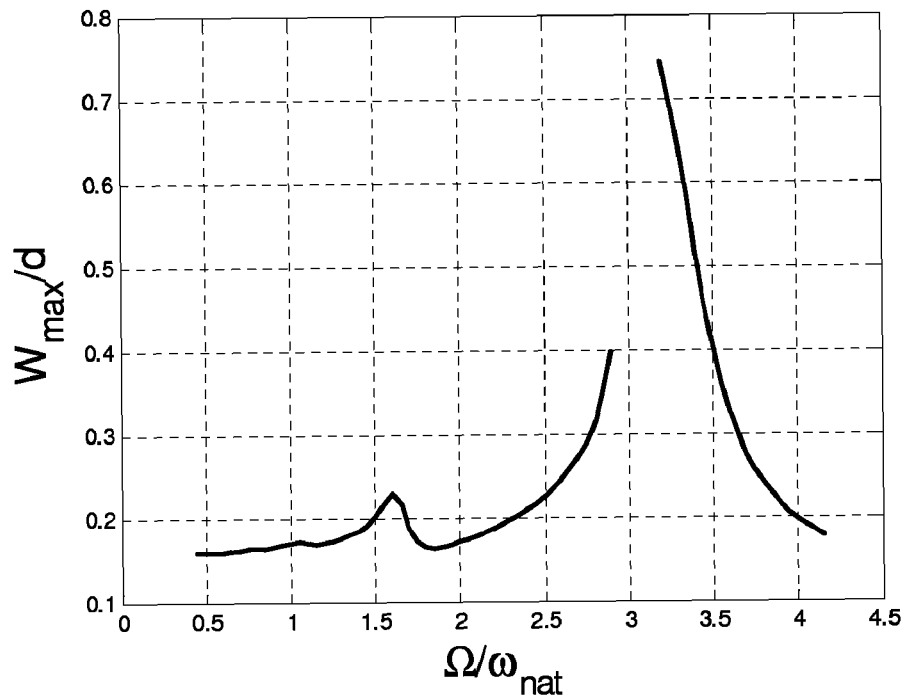
FIG. 5 shows the maximum displacement of a cantilever beam of a parallel-plate capacitor versus the frequency of excitation.
Figure 6:
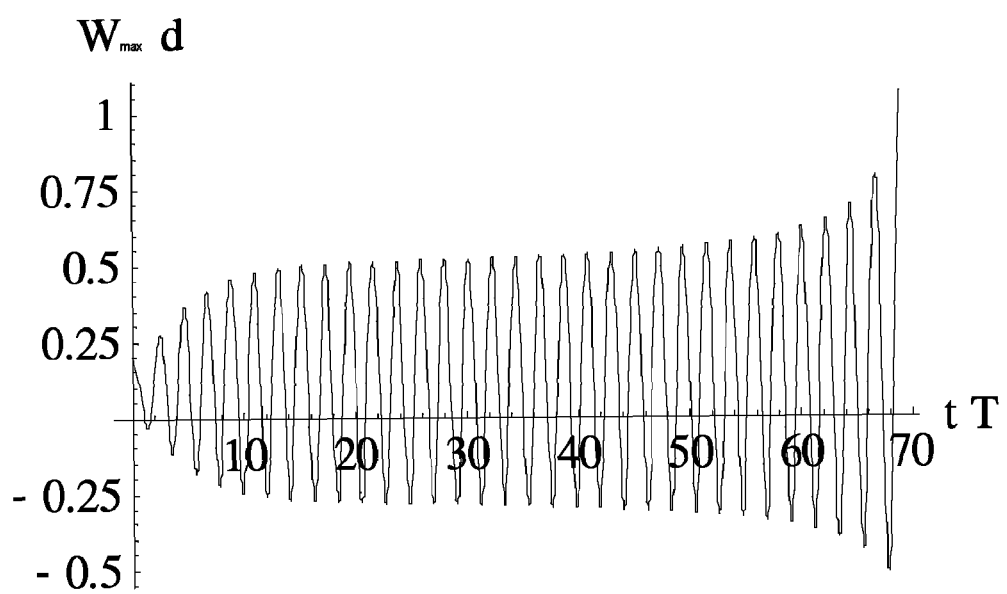
FIGS. 6 and 7 show a time history response of the microbeam when excited by different frequencies.

The pull-in voltage for the microbeam when actuated by a DC voltage only is $V_{DC}=0.6$ V. If this microbeam is excited by $V_{DC}=0.4$ V and an AC harmonic load of amplitude $V_{AC}=0.1$ V, a dynamic pull-in occurs when the excitation frequency $\Omega$ is close to the natural frequency of the microbeam, that is $\Omega/\omega_{nat}=\omega_{natural}/\omega_{nat}=3.3$. This is demonstrated in FIG. 5, which shows the maximum displacement of the cantilever beam $W_{max}$ normalized by the gap width d underneath the beam versus the excitation frequency $\Omega$ normalized by $\omega_{nat}$. FIG. 5 shows that when $\Omega$ gets close to $\omega_{natural}$ ($\Omega=3.3\,\omega_{nat}$), resonance occurs and $W_{max}$ reaches its peak. Because of the presence of the instability threshold pull-in, the frequency-response curve opens up. We note that there is band of frequency near this regime where there is no stable state for the microbeam exists. We can call this band the "pull-in band". If the microbeam is excited near this range of frequency, it will snap down and go to pull-in. On the other hand, if the microbeam is excited at a frequency away from this pull-in band, the microbeam will oscillate in a stable motion and never goes to pull-in. FIG. 6 shows these cases.

FIG. 5 shows the maximum displacement of a cantilever beam of a parallel-plate capacitor versus the frequency of excitation. Here, $V_{DC}=0.4$ V and $V_{AC}=0.1$ V.

FIG. 6 shows a time history response of the microbeam when excited by $\Omega=3$, which is in the pull-in regime. It is clear that the response is unstable and it goes to pull-in, where $W_{max/d}$ is equal one.

Figure 7:
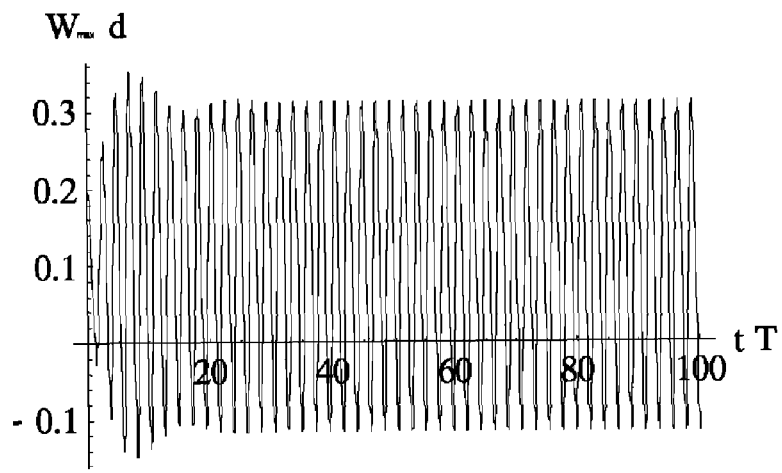

FIG. 7 shows a time history response of the microbeam when excited by $\Omega=2.6$, which is away from the pull-in regime. It is clear that the response is stable and it reaches a steady-state value $W_{max}/d$ equal 0.3.

The cantilever microbeam can be coated with a sensing material, such as some "smart" polymers that are sensitive to specific gases. (See references incorporated herein by reference supra). Hence, the microbeam becomes as a chemical sensor to that gas. The coated sensitive surface layer of the cantilever beam can absorb a small amount of specific gas, which is around in the environment. This increases the weight of the cantilever beam, which leads to a decrease in its natural frequency, since it is proportional to the inverse of the square root of the mass of the beam (if the stiffness of the microbeam is denoted by k, then $\omega_{nat}=\sqrt{k/m}$). This shift in frequency can be considered as an indication to the presence of the gas in the environment. This is effect is well known. A sensing is possible of any condition which directly or indirectly changes the relevant mechanical characteristics of the beam, such as its mass, stiffness, size, resonant frequency, damping, or the like. In the case, for example, of a swellable polymer, the mechanical separation of the plates may be changed in dependence on a concentration or presence of an analyte. Other configurations are possible, as well, so it should be understood that the scope of the invention is not limited to a sensor formed by an absorptive coating on a microcantilever beam altering the resonant frequency thereof.

The principle of operation of an embodiment of the device relies on the above principle of gas sensors and the dynamic pull-in concept demonstrated in the previous section. According to the present invention, the microbeam is excited by a combination of DC load and AC load such that the microbeam normally operates below the dynamic pull-in band of frequency.

When the microbeam is subject to the existence of the specific gas or other substance desired to be detected, which absorbs to the beam or a coating thereon, its mass will increase, and its natural frequency will decrease. This will decrease the ratio $\Omega/\omega_{nat}$, and hence the operating point on the frequency response curve will shift to the right. We can calibrate this shift such that the shifted $\Omega/\omega_{nat}$ lies in the dynamic pull-in frequency band. Hence, the microbeam collapses, to close an electric circuit to indicate the presence of the gas and at the same time to send an electrical signal, which can be used for alarming or any other useful function. In some cases, the collapse is a reversible process, and therefore a decrease in a concentration of a material can be sensed by an opening of the switch.

Figure 8:
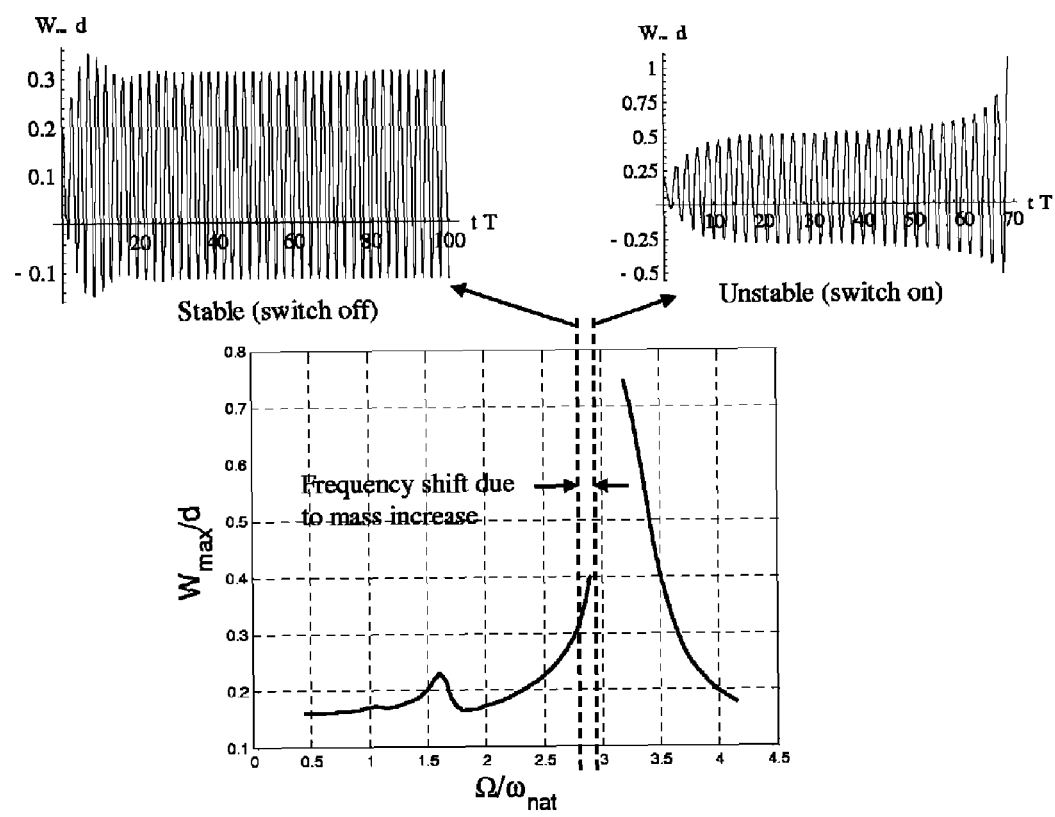
FIGS. 8 and 9 show the operating principle a switch in accordance with the present invention as a gas sensor.
Figure 9:
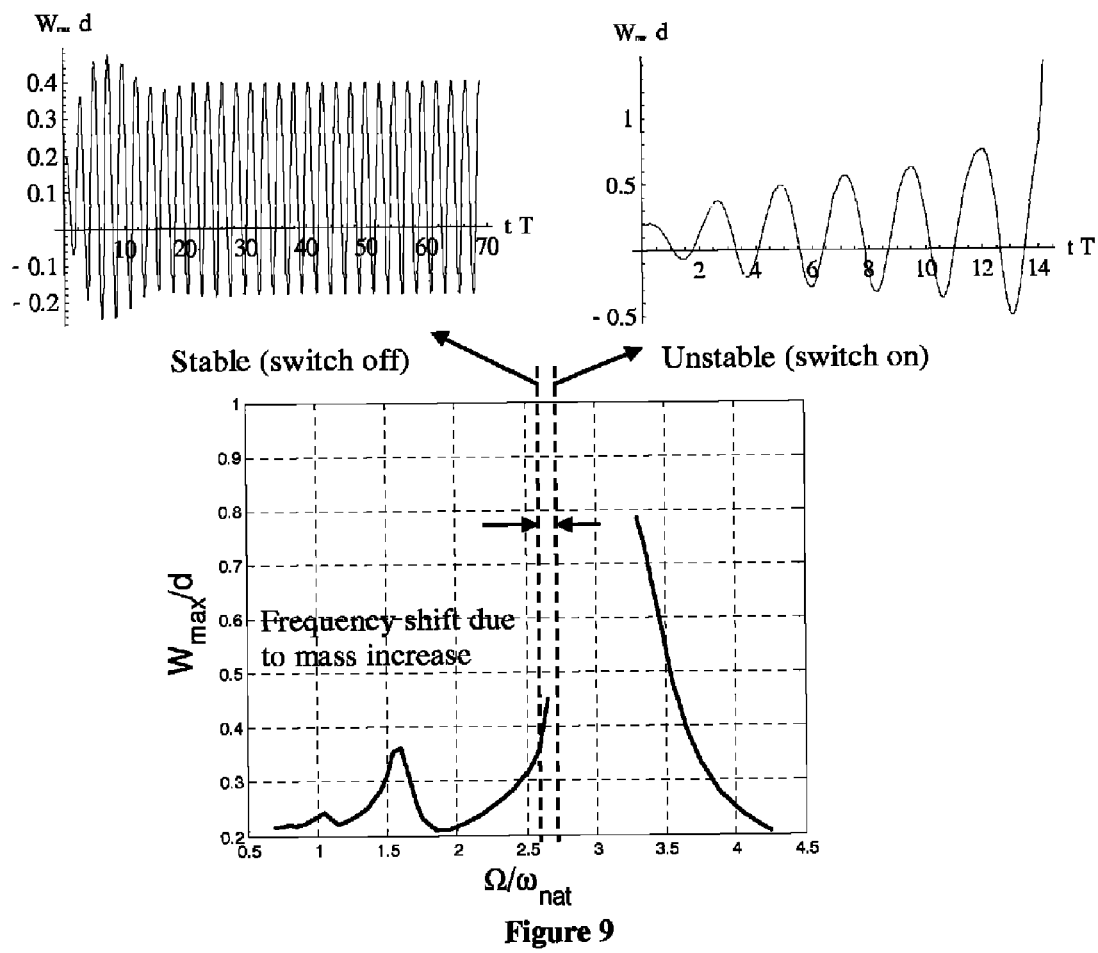

FIGS. 8 and 9 illustrate the principle of operation. FIG. 8 shows the operating principle of a switch in accordance with the present invention. The microbeam is biased by a DC voltage equal 0.4 V and an AC load equal 0.1 V. The dashed line to the left represents the operating point of the microbeam before the mass detection. The dashed line to the right represents the operating point of the microbeam after detecting a gas, which increase its mass by 10%.

FIG. 9 shows the switch when biased by a DC voltage equal 0.4 V and an AC load equal 0.15. The dashed line to the left represents the operating point of the microbeam before the mass detection. The dashed line to the right represents the operating point of the microbeam after detecting a gas, which increase its mass by 5%.

Figure 10:
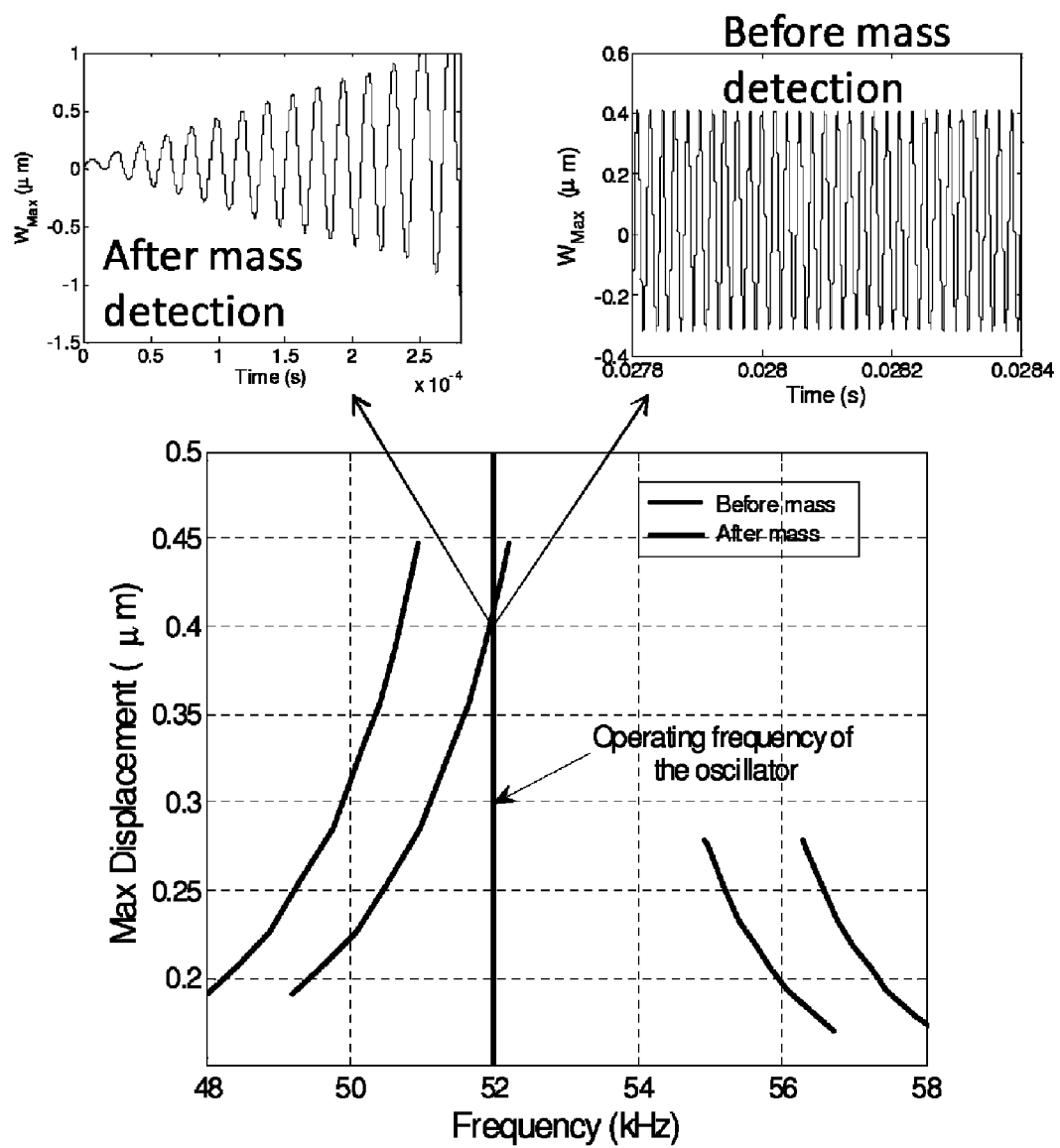
FIG. 10 shows dimensional frequency-response curves for a clamped-clamped microbeam before and after 5% mass increase, and two time history simulations for the response of the microbeam before and after mass detection.

FIG. 10 shows dimensional frequency-response curves for a clamped-clamped microbeam (i.e., one which is supported on opposite sides, and which therefore has a degree of freedom for movement between the supported sides) before and after a 5% mass increase.

This scenario is illustrated using dimensional quantities and plots. Consider the case in which the microbeam is initially excited by a combination of a DC and AC harmonic load of a fixed frequency below the escape band, for example at 52 kHz in FIG. 10. Assuming a 5% increase in mass because of external mass detection/absorption, this leads to a decrease in its natural frequency shifting it to the left. This means that the whole frequency-response curve of the microbeam shifts to the left too. By maintaining the frequency of excitation fixed at 52 kHz, while the microbeam's natural frequency shifting to smaller values, and by calibrating this shift such that the operating frequency lies in the escape band after mass detection, the microbeam will be forced to pull-in. Hence, it can act as a switch to close an electric circuit, and, for example, pass a low impedance electric signal.

FIG. 10 also shows a simulated time history response for the microbeam for two states, before and after mass detection. Prior to mass detection, the microbeam oscillates at a steady-state amplitude of 0.4. After mass detection, the microbeam undergoes unstable oscillation leading to its collapse after 0.25 ms.

The microbeam thus normally is driven to operate close to the instability tongue, and the perturbation caused by a change in mechanical properties causes the microbeam to enter the instability tongue and collapse. This collapse, in turn, permits a switching action dependent on a physical contact of the microbeam and the back plate.

Figure 11:
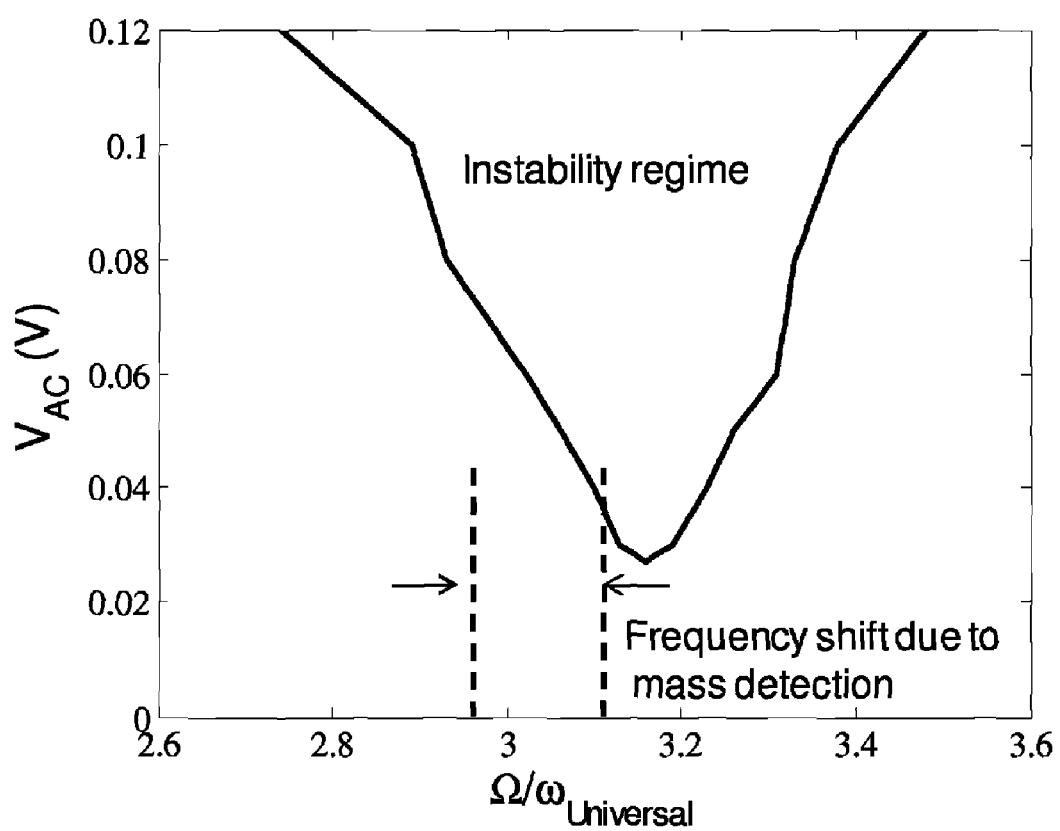
FIG. 11 shows the instability tongue of an electrically actuated cantilever beam.

FIG. 11 shows a calculated instability tongue for a cantilever microbeam for the case of Q=100 as a function of $V_{AC}$ and $\Omega/\omega_{Universal}$. The figure also illustrates the operating principle based on primary-resonance excitation.

The present invention can operate as a chemical sensor or a biosensor. In the case of a biosensor, typically the sensor component itself provides a biochemical specificity for binding or catalyzing a reaction, for example. It can be used to detect explosive, hazardous, or any other gases or substances, and to activate/actuate alarming or defensive systems. The invention also may be used to detect biological agents, such as bacteria and viruses, in the environment or in the human body and then send a signal indicating their existence, and may be to perform other functions.

Since other modifications and changes varied to fit particular operating requirements and environments will be apparent to those skilled in the art, this invention is not considered limited to the example chosen for purposes of this disclosure, and covers all changes and modifications which does not constitute departures from the true spirit and scope of this invention.

Having thus described the invention, what is desired to be protected by Letters Patent is presented in the subsequently appended claims.

What is claimed is:

1. A switch, comprising:
   a mechanically resonant first element;
   an electric field generator, configured to produce an electric field which selectively subjects the first element to a force having at least one dynamic component adapted to excite an oscillation in the first element, and a biasing component adapted to induce a force which biases the first element with respect to a second element; and
   a material which selectively alters at least one mechanical condition, tending to cause a change in an oscillation of the first element,
   wherein the material is configured to provide a range of alteration in the at least one mechanical condition which includes an unstable oscillation behavior which causes a dynamic pull-in and a contact between the first and second elements, and
   wherein the first element has a stable oscillation state and an unstable oscillation state, and wherein the electric field generator is configured to oscillate the first element in the stable oscillation state absent an alteration of the mechanical condition by the material within a potential well defined by the electrostatic field, and the material is further configured to alter the mechanical condition such that the oscillation of the first element enters the unstable oscillation state and escapes from the potential well, resulting in a dynamic pull-in of the first element in the unstable oscillation state.

2. The switch according to claim 1, wherein a contact state between the first element and the second element is dependent on a chemical condition.

3. The switch according to claim 1, wherein the material alters an effective mass of the first element by interaction with an external influence, altering a resonance property of the first element.

4. The switch according to claim 1, wherein the first element comprises a cantilever beam.

5. The switch according to claim 1, wherein the material comprises a polymer which selectively absorbs an analyte.

6. The switch according to claim 1, wherein the material comprises a sensing material responsive to an analyte, and a contact between the first and second elements is selectively dependent on a concentration of the analyte.

7. The switch according to claim 1, wherein the material comprises a sensing material responsive to an analyte, and a contact between the first and second elements is selectively dependent on an amount of the analyte.

8. The switch according to claim 1, wherein the material comprises a sensing material responsive to an analyte, and a contact between the first and second elements is selectively dependent on a change in the analyte.

9. The switch according to claim 1, wherein the contact between the first and second elements is reversible.

10. The switch according to claim 1, wherein the contact between the first and second elements causes the first and second elements to stick together after a condition which cause contact to occur is removed.

11. The switch according to claim 1, wherein the biasing component comprises a static electrostatic field configured to displace the first element with respect to the second element.

12. The switch according to claim 1, wherein the dynamic component comprises a dynamic electrostatic field configured to oscillate the first element at a frequency near a lowest resonant frequency of the first element.

13. The switch according to claim 1, wherein the dynamic component comprises a dynamic electrostatic field configured to oscillate the first element at a frequency near a higher order resonant frequency of the first element.

14. The switch according to claim 1, further comprising an output configured to convey a signal corresponding to a state of contact between the first element and the second element.

15. The sensor according to claim 1, wherein the second element is configured to form a conductive path upon contact with the first element, further comprising an electrical lead extending from each of the first and second elements.

16. The sensor according to claim 1, wherein a contact state between the first element and the second element is dependent on a biological condition.

17. The switch according to claim 1, wherein the first element comprises a clamped-clamped beam fixed at opposing ends and configured to oscillate between the fixed ends.

18. The sensor according to claim 1, wherein the sensor is reusable after contact between the first element and the second element.

19. The sensor according to claim 1, wherein an irreversible mechanical change occurs upon a contact between the first element and the second element.

20. The sensor according to claim 1, wherein the first element is fabricated from silicon.

21. The sensor according to claim 1, wherein the material is selectively responsive to a concentration of a gas in contact with the material.

22. The sensor according to claim 1, wherein the material is selectively responsive to an explosive material.

23. The sensor according to claim 1, wherein the material alters the mechanical condition by a change in at least one of a change in mass, stiffness, size, resonant frequency, and damping.

24. The switch according to claim 1, where in the first element is configured to serve as an electrode for the electric field generator.

25. The switching structure according to claim 1, wherein the at least one dynamic component produced by the electric field generator comprises a constant non-zero amplitude and waveform AC voltage, and the biasing component comprises a constant non-zero DC bias voltage, and the dynamic pull-in and the contact between the first and second elements persists over a plurality of AC voltage waveform cycles of the AC voltage.

\* \* \* \* \*